(12) United States Patent
Potts

(10) Patent No.: US 6,436,663 B1
(45) Date of Patent: Aug. 20, 2002

(54) METHOD FOR THE SIMULTANEOUS DEMONSTRATION OF VARIOUS OPPORTUNISTIC PATHOGENS

(75) Inventor: Mark H. Potts, Williamsfield, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/709,437

(22) Filed: Nov. 13, 2000

(51) Int. Cl.⁷ .................................................. G01N 1/30
(52) U.S. Cl. ........................ 435/40.5; 435/4; 435/40.51; 435/40.52
(58) Field of Search ........................... 435/40.52, 40.51, 435/40.5, 4

(56) References Cited

U.S. PATENT DOCUMENTS 4,906,451 A    3/1990  Sims ............................ 435/30
5,242,820 A    9/1993  Lo et al. ................... 435/40.52
5,614,376 A    3/1997  Copley et al. ........... 435/252.1

OTHER PUBLICATIONS

Mowry et al. Am, J. Pathol. (1959), 35, 708–9.*

\* cited by examiner

*Primary Examiner*—Jean C. Witz
*Assistant Examiner*—Brett Ozga
(74) *Attorney, Agent, or Firm*—Barry A. Edelberg; A. David Spevack; Thomas E. McDonnell

(57) ABSTRACT

A method of simultaneously staining for various opportunistic pathogens stains tissues sections with Ziehl-Neelsen carbo-fuchsin, Schiff reagent, and a mixture of metanil yellow and stock fast green solution. In particular, the method is useful for staining tissue sections suspected of containing opportunistic pathogens commonly found in AIDS patients, i.e., acid fast mycobacteria, fungus, and *Pneumocystis carinii*.

8 Claims, No Drawings

METHOD FOR THE SIMULTANEOUS DEMONSTRATION OF VARIOUS OPPORTUNISTIC PATHOGENS

Background of the Invention

1. Field of the Invention

The present invention relates generally to the simultaneous demonstration of diverse opportunistic pathogens and more specifically to methods for simultaneous staining for diverse opportunistic pathogens.

2. Description of the Background Art

Previously, three different stains had to be performed by the histology technician to help the pathologist identify these three different organisms commonly found in AIDS victims. These stains would include a Ziehl-Neelsen stain for acid fast mycobacteria (cause of tuberculosis), a Grocott Methenamine Silver Procedure and/ or a Periodic Acid Schiff stain for fungus, and a Grocott Methenamine Silver stain for *Pneumocystis carinii*. (*Pneumocystis carinii* has a longer staining time than fungus and must be stained separately). If using the Grocott Methenamine Silver technique however for staining fungus or *Pneumocystis carinii*, there are some disadvantages to consider. With the ever increasing Environmental Protection Agency restrictions on what types of waste can or can not be discarded down regular sewage systems, this becomes a factor in performing such stains using heavy metals such as silver stains. These types of stains must now be collected and classified as "Hazardous Waste" and must be treated and discarded properly which costs time and money.

Another disadvantage of using silver stains for fungus or *Pneumocystis carinii* is that they are generally lengthy and time-consuming procedures if not using a microwave technique. The Grocott Methenamine Silver (GMS) technique requires 11 different staining solutions and 15 staining steps. Time must also be taken periodically to prepare fresh the methenamine-silver nitrate solution each time the stain is used. In addition, the slides must be checked periodically while in the silver solution to check for proper staining intensity. Generally these procedures take from 2 to 3 hours to complete.

Yet another disadvantage of using a GMS technique is that if you are staining a lung biopsy from a known AIDS patient, the pathologist most likely is looking for either fungus or *Pneumocystis carinii* in the lung, sometimes both. To stain for both of these organisms, you have to perform 2 different GMS stains. The exposure time in the silver solution is shorter if staining for fungus, but not long enough to stain the *Pneumocystis carinii* organism, and if staining for P. carinii, any fungus that may be present will be overexposed to the silver solution, distorting its important morphology. Also when staining for fungus or Pneumocystis, the pathologist will usually include a Ziehl-Neelsen stain for acid fast mycobacteria. This constitutes the three different stains normally used.

SUMMARY OF THE INVENTION

Accordingly, it is an object of this invention to simultaneously stain a variety of different opportunistic pathogens on a single slide.

It is another object of the present invention to minimize the number of steps required to stain a mixture including a variety of different opportunistic pathogens.

It is a further object of the present invention to minimize the time and expense required to stain a mixture including a variety of different opportunistic pathogens.

It is yet another object of the present invention to improve staining quality by minimizing background staining that might otherwise mask the presence of opportunistic pathogens.

It is a yet further object of the present invention to minimize the use of silver and other heavy metals in staining methods for opportunistic pathogens.

These and additional objects of the invention are accomplished by a combination of various staining steps including the use of a new staining solution. Sections stained in cabol-fuchsin are oxidized in chromic acid, exposed to sodium bisulfite, and then further oxidized in periodic acid before staining with Schiff reagent. The Schiff reagent-stained section is then counterstained in a new staining solution, referred to in the following specification and claims and "Potts Green". As used throughout the specification and the claims that follow, "Potts Green" is a staining solution including about 15–25 volume percent stock fast green solution and 75–85 volume percent metanil yellow solution.

DESCRIPTION OF THE PREFERRED EMBODIMENTS

Unless stated otherwise, the procedures are typically performed at room temperature. While these procedures may be performed at lower or higher temperatures, such temperature changes may require modification of the stated treatment times to achieve optimal results. These optimizations for different processing temperatures may be determined empirically by those skilled in the art without undue experimentation. Typically, the tissue stained in the present invention are obtained from paraffin embedded tissue section. Traditionally, and in the method of the present invention, the sections are cut at a sufficient thinness to allow slide mounting and microscopic examination, and yet cut sufficiently thick that they may be readily handled. Typically, these section have a thickness of about 4 to about 5 $\mu$m As with standard staining procedures, the sections are deparaffinized and hydrated to distilled water before initial staining.

The Ziehl-Neelsen carbol-fuchsin solution used in initial step of the method of this invention is a standard, well-known solution and may be purchased commercially. The Ziehl-Neelsen carbol-fuchsin staining step is carried out using the standard procedures for this stain. That is, the sections are exposed to the Ziehl-Neelsen carbol-fuchsin solution sufficiently long to stain any acid fast mycobacteria in the sample. Overstaining, however, increases background staining, needlessly increases processing time, and should be minimized or avoided. At room temperature, typical staining times range from about 30 to about 60 min, and more typically from about 30 to about 45 min.

After staining with Ziehl-Neelsen carbol-fuchsin, the section is washed with water to remove excess stain. The section may be initially washed in tap water, followed by rinsing in distilled water to remove chlorination and other contaminants from the tap water.

After rinsing, the sections are typically decolorized to reduce background staining. Usually, a 70% acid alcohol (typically a 70 vol % aqueous solution of methanol-denatured ethanol, about 1 vol % acid to decolorize the carbol-fuchsin stain). The decolorized section is washed in tap water to remove the acid alcohol decolorizer.

After rinsing, the decolorized section is oxidized in a first oxidizer, such as 10% (weight/volume %) chromic acid for a sufficient time to oxidize Pneumocystis organisms. Typically, this requires about 10 minutes at room temperature. Shorter times may not achieve the required oxidation, while longer time may decolorize the mycobacteria (acid-fast bacilli, also referred to as AFB). The oxidized tissue section is then washed in running tap water until the yellow color of the section (indicating the presence of chromic acid) disappears.

After initial oxidation and rinsing, the oxidizing agent must be thoroughly neutralized and/or removed. Where the initial oxidizing agent is chromic acid, oxidation/neutralization may be achieved, for example, by placing the sections in a 1 w/v % aqueous solution of sodium bisulfite for about 1 min. Longer treatments with sodium bisulfite will merely increase processing time without noticeably improving results. The sodium bisulfite may then be removed from the section, for example, by rinsing in distilled water. Typically, three changes of distilled water are sufficient to remove the sodium bisulfite.

After rinsing removes the sodium bisulfite, the section is then oxidized with a second oxidizer, such as 1 weight/volume % periodic acid to complete oxidation of fungal elements, which allows subsequent staining of those fungal elements with Schiff reagent. Rinsing in distilled water (typically at least three changes), removes the oxidizer.

The section is then stained in Schiff reagent for about 15 to about 20 min. Overly long stain times can result in undesirable magenta background staining. After staining with Schiff reagent, the section is rinsed, for example in tap water, for about 5 to 10 minutes. Rinsing in tap water for an extended time can cause the stain to fade due to chlorination. The section is then rinsed in distilled water, typically at least three changes.

After Schiff stain and rinsing, the section is then stained in Potts Green solution for about 30 sec to one minute. Too short of a staining time will provide insufficient staining. Overly long staining time will result in background staining and mask organisms. After staining with Potts Green, the section is dehydrated in about 2 to three changes of absolute or denatured ethanol, followed by clearing with a clearant (e.g., xylene, limonene, etc.). Water should be avoided at this stage because it can wash out the yellow coloring in the Potts Green staining solution. The dehydrated section may then be mounted in a resinous mounting medium typically used for mounting sections.

Having described the invention, the following examples are given to illustrate specific applications of the invention including the best mode now known to perform the invention. These specific examples are not intended to limit the scope of the invention described in this application.

EXAMPLES

MATERIALS AND METHODS

FIXATION:
10% Neutral Buffered Formalin
EQUIPMENT:
Coplin jars
Filter paper
Funnel
Gloves
Microscope
Forceps
TECHNIQUE:
Cut paraffin sections at 4–5 microns
QUALITY CONTROL:

Sections of tissues containing known AFB, fungus, and *Pneumocystis carinii* were used. Note: All 3 of these controls may be fixed on the same slide to ease number of slides to be stained.

| REAGENTS: | |
|---|---|
| ZIEHL-NEELSEN CARBOL FUCHSIN SOLUTION (May be bought commercially) | |
| Phenol crystals (melted) | 2.5 ml |
| Absolute alcohol | 5.0 ml |
| Basic Fuchsin | 0.5 gm |
| Distilled water | 50.0 ml |
| 1% ACID ALCOHOL SOLUTION | |
| Hydrochloric acid, concentrated | 1.0 ml |
| 70% alcohol | 100.0 ml |
| 70% ALCOHOL SOLUTION | |
| 100% ethanol | 70.0 ml |
| Distilled water | 100.0 ml |
| 10% CHROMIC ACID SOLUTION | |
| Chromium Trioxide crystals | 10.0 gm |
| Distilled water | 100.0 ml |
| 1% SODIUM BISULFITE SOLUTION (May be bought commercially) | |
| Sodium Bisulfite | 1.0 gm |
| Distilled water | 100.0 ml |
| 1% PERIODIC ACID SOLUTION (May be bought commercially) | |
| Periodic Acid crystals | 1.0 gm |
| Distilled water | 100.0 ml |
| SCHIFF REAGENT (May be bought commercially) | |
| Distilled water | 800.0 ml |
| Basic Fuchsin | 4.0 gm |
| Sodium Metabisulfite | 4.0 gm |
| 1 N Hydrochloric Acid | 80.0 ml |
| Activated Charcoal | 2.0 gm |

Water to was heated to the boiling point and then removed from the flame. Basic fuchsin was added and the resulting solution was again heated to the boiling point. The solution was cooled to 50 degrees C., then filtered. 80.0 ml of 1 N HCl were added, and the solution was then cooled completely. To the cooled and 4.0 gm of sodium metabisulfite was added. The solution was left to stand in the dark overnight; it turned light amber. 2.0 gm activated charcoal were added and the solution was shaken for 1 minute. The solution was filtered and the filtrate stored in the refrigerator. The stored solution was tested for quality of Schiff Reagent before use. 10 ml of 37% to 40% formaldehyde were placed in a beaker or Erlenmeyer flask. A few drops of Schiff Reagent was added. If the solution rapidly turns reddish purple, it is considered good. If the reaction was delayed and the resultant color was a deep blue-purple, the solution was breaking down and was not be used.

| STOCK FAST GREEN SOLUTION | |
|---|---|
| Fast Green FCF (C.I. 42053) | 0.2 gm |
| 0.2% Acetic Acid solution | 100.0 ml |
| 0.2% ACETIC ACID SOLUTION | |
| Glacial Acetic Acid | 0.2 ml |
| Distilled water | 99.8 ml |
| METANIL YELLOW SOLUTION | |
| Metanil Yellow (C.I. 13065) | 0.25 gm |
| Distilled water | 100.0 ml |
| Glacial Acetic Acid | 0.25 ml |
| POTTS GREEN SOLUTION | |
| Stock Fast Green Solution | 1 part |
| Metanil Yellow solution | 4 parts |

PROCEDURE:
1. Tissue sections were deparaffinized and hydrated to distilled water.
2. The deparaffinized sections were stained sections in freshly filtered Ziehl-Neelsen carbol-fuchsin for 30 minutes.
3. The stained sections were then washed well in running tap water.
4. The washed sections were rinsed in 3 changes of distilled water.
5. The rinsed slides were then decolorized individually in 70 vol/vol % acid alcohol.
6. The decolorized slides were washed well in running tap water.
7. The washed and decolorized slides were then placed slides in first oxidizer (10% chromic acid solution) for 10 minutes.
8. The initially oxidized slides were again washed well in running tap water until yellow color of section disappears.
9. After washing, the initially oxidized sections were placed in 1% sodium bisulfite solution for 1 minute.
10. The sodium bisulfite-treated sections were then rinsed in 3 changes of distilled water.
11. The rinsed sodium-bisulfite-treated slides were then placed in a second oxidizer (1% periodic acid solution) for 3 minutes.
12. The twice oxidized sections were then rinsed in 3 changes of distilled water.
13. The rinsed and twice oxidized sections were then stained in Schiff reagent for 15–20 minutes.
14. The Schiff reagent-stained sections were then washed in running tap water for 5–10 minutes.
15. After washing, the Schiff reagent-stained sections were rinse in 3 changes of distilled water.
16. The rinsed and washed, Schiff reagent-stained sections were then counterstained in Potts Green solution for 30 seconds to 1 minute.
17. The counterstained sections were then dehydrated through 2 changes of absolute alcohol and clearant.
18. The dehydrated sections were then mounted in resinous mounting medium.

RESULTS:

| | |
|---|---|
| Acid fast mycobacteria | bright red |
| Fungal walls | magenta |
| Histoplasma fungal elements | light pink |
| *Pneumocystis carinii* | purple-red |
| Red blood cells | yellow-green |
| Other tissue elements | blue-green |

Obviously, many modifications and variations of the present invention are possible in light of the above teachings. It is therefore to be understood that, within the scope of the appended claims, the invention may be practiced otherwise than as specifically described.

What is claimed is:

1. A method of simultaneously staining opportunistic pathogens, comprising the steps of:

staining a section of tissue suspected of containing opportunistic pathogens in Ziehl-Nelson carbol-fuchsin;

decolorizing said carbol fuchsin stained section in acid alcohol;

oxidizing said decolorized section in an aqueous chromic acid solution for a time sufficient to oxidize any Pneumocystis bacteria present in said section;

exposing said oxidized section to an aqueous solution of sodium bisulfite aqueous solution;

further oxidizing said sodium bisulfite-treated section in an aqueous periodic acid solution for a sufficient time to complete oxidation of any fungus present in said section;

staining said periodic acid-oxidized section in Schiff reagent;

counterstaining said section in Potts Green solution.

2. The method of claim 1, wherein said chromic acid solution is about 10 weight/volume % chromic acid.

3. The method of claim 1, wherein said sodium bisulfite solution is about 1 weight/volume % sodium bisulfite.

4. The method of claim 1, wherein said periodic acid solution is about 1 weight/volume periodic acid.

5. The method of claim 1, further comprising the step of dehydrating, in absolute alcohol, said counterstained sections.

6. The method of claim 1, wherein said method simultaneously stains Pneumocystis, acid fast mycobacteria, and fungus.

7. The method of claim 1, wherein said Potts Green solution comprises about 15–25 volume percent stock fast green solution and about 75–85 volume percent metanil yellow solution.

8. The method of claim 7, wherein said Potts Green solution comprises about 20 volume percent stock fast green solution and about 80 volume percent metanil yellow solution.

* * * * *